(12) United States Patent
Kvasnik et al.

(10) Patent No.: US 7,856,863 B2
(45) Date of Patent: Dec. 28, 2010

(54) BREATH SAMPLING DEVICE

(75) Inventors: Frank Kvasnik, Marple (GB); Stephen Robert Smirk, Manchester (GB)

(73) Assignee: Sensam Limited, Marple (GB)

( * ) Notice: Subject to any disclaimer, the term of this patent is extended or adjusted under 35 U.S.C. 154(b) by 263 days.

(21) Appl. No.: 11/921,859

(22) PCT Filed: Jun. 13, 2006

(86) PCT No.: PCT/GB2006/002133

§ 371 (c)(1),
(2), (4) Date: Dec. 10, 2007

(87) PCT Pub. No.: WO2007/000568

PCT Pub. Date: Jan. 4, 2007

(65) Prior Publication Data

US 2009/0044597 A1    Feb. 19, 2009

(30) Foreign Application Priority Data

Jun. 25, 2005   (GB) ................... 0512987.9

(51) Int. Cl.
*G01N 1/22*    (2006.01)
*G01N 33/98*   (2006.01)

(52) U.S. Cl. .................... 73/23.2; 73/23.34; 73/864.51; 73/864.83; 73/864.91

(58) Field of Classification Search ............ 73/23.2, 73/23.3–23.34, 863, 864.33, 864.51, 864.83, 73/864.91
See application file for complete search history.

(56) References Cited

U.S. PATENT DOCUMENTS

| | | | |
|---|---|---|---|
| 3,544,273 A | 12/1970 | McConnaughey | |
| 3,613,665 A * | 10/1971 | Gorsuch | 600/543 |
| 3,676,073 A * | 7/1972 | Luckey | 436/178 |
| 4,046,015 A * | 9/1977 | Riedl et al. | 73/864.91 |
| 4,277,251 A | 7/1981 | Leichnitz | |
| 4,492,673 A * | 1/1985 | Eriksen et al. | 422/85 |
| 4,740,475 A * | 4/1988 | Paul | 436/165 |
| 5,171,535 A * | 12/1992 | Lamont | 422/85 |
| 5,174,959 A * | 12/1992 | Kundu et al. | 422/59 |
| 5,361,772 A | 11/1994 | Murnick et al. | |
| 5,432,094 A | 7/1995 | Delente et al. | |
| 5,826,577 A | 10/1998 | Perroz | |
| 5,834,626 A | 11/1998 | De Castro | |

(Continued)

FOREIGN PATENT DOCUMENTS

DE    200 01 995    8/2000

(Continued)

*Primary Examiner*—David A. Rogers
(74) *Attorney, Agent, or Firm*—Dennison, Schultz & MacDonald (57) ABSTRACT

A hollow container defining a sample chamber is formed of at least two parts which fit together and have apertures therein. One of the parts is displaceable relative to the other part between a first relative disposition of the parts in which the apertures are open so as to provide a clear path for air to pass through the container and a second relative disposition of the parts in which the apertures are closed so that there is no path for air to pass through and a volume of air is trapped in the chamber. In one embodiment part is axially moveable relative to the other part. In another embodiment where the parts are tubular, one of the parts is rotatable relative to the other.

8 Claims, 5 Drawing Sheets

U.S. PATENT DOCUMENTS 6,177,051 B1 * 1/2001 Kimelman .................... 422/85
6,244,117 B1 * 6/2001 Mengel et al. ............ 73/863.21
7,284,412 B1 * 10/2007 Perrault ......................... 73/40
7,285,246 B1 * 10/2007 Martin ........................ 422/86

FOREIGN PATENT DOCUMENTS

| EP | 0 133 326 | 2/1985 |
| WO | WO 96/32062 | 10/1996 |
| WO | WO 2004/058064 | 7/2004 |

* cited by examiner

BREATH SAMPLING DEVICE

This application is a 371 of PCT/GB2006/002133 filed on Jun. 13, 2006.

The present invention relates to a device for use in testing for the presence of a substance in a sample of gas exhaled by a person. In certain embodiments the invention may be used to detect ammonia in the breath of patients suffering from *Helicobacter pylori* infection.

Breath sampling is often carried out in a clinical context, as a non-invasive diagnostic tool. A sample of gas exhaled by a person is tested for the presence of a substance known to indicate a particular underlying condition.

It is now widely accepted that bacterial infection by *H. Pylori*, discovered approximately 20 years ago, leads to peptic ulcers that affect around 1 in 10 people at some time in their lives, with many more suffering from gastritis. Non-invasive screening for these bacteria may be carried out using breath samples, often collected in a doctor's surgery and sent for analysis in an outside laboratory. Typically a patient provides a breath sample in order to determine a base level of carbon 13 dioxide or carbon 14 dioxide ($^{13}CO_2$ or $^{14}CO_2$) present in the exhaled breath due to ingestion of certain foods. The patient is then administered an activating substance, $^{13}C$ or $^{14}C$-labelled urea, and, after a suitable period has elapsed to allow the ingested urea time to contact any *H. Pylori* in the gastro intestinal tract, a second breath sample is taken, and tested for the presence of $^{13}CO_2$ or $^{14}CO_2$. *H Pylori* excretes an enzyme, urease, which catalyses the breakdown of urea into ammonia ($NH_3$) and carbon dioxide, and which, under normal circumstances, is not present in the human body. If a patient is infected with *H. Pylori* bacteria, the second sample obtained after ingestion of the urea would be expected to exhibit a greater quantity of $^{13}CO_2$ or $^{14}CO_2$ than the first or "control" sample taken to establish the base level of $^{13}CO_2$ or $^{14}CO_2$ in the patient's body.

A newer test for *H. Pylori* infection is based on the detection of ammonia in the breath samples supplied by the patient, rather than $^{13}CO_2$ or $^{14}CO_2$. In a similar way to the $CO_2$ test, a patient firstly provides a control breath sample in order to determine a base level of ammonia present in the exhaled breath, due to "normal" causes, such as ingestion of certain foods, or due to other conditions, unrelated to *H. Pylori* infection, such as renal failure or certain oral and dental conditions which may result in ammonia production.

A device for collecting a breath sample is disclosed in EP 1149557 A2 in the form of an inflatable bag into which a patient exhales to provide a breath sample. The device incorporates an indicator, which is arranged to contact a breath sample collected in the bag. The indicator changes colour when a given substance to be detected is present in the sample thereby providing a visible indication as to its presence.

Known systems for detection of ammonia in breath samples suffer from certain practical drawbacks. In particular, this is due to the fact that the level of ammonia in a breath sample is typically only a few ppm. Consequently, devices such as that described in EP 1149557 A2 cannot be used for this application since colour changes of an indicator at these low concentrations are not sufficiently strong to be detected by eye. External devices (for example spectrophotometers) need to be used to determine and quantify any change in the colour of the indicator that is used in a gas sampling device for this particular purpose and it is necessary to remove the indicator from the gas sampling device and present it to the colour-measuring device.

An object of the present invention is to provide a sample collecting device for use by a non-specialist operator in an integrated system which allows the presence of a substance (particularly ammonia, but not exclusively so) in a breath sample to be more easily and accurately detected than hitherto.

A further object is to provide a sample collecting device which allows differences between amounts of a substance in a breath sample to be more easily and accurately determined than hitherto.

It is desirable to collect, for purposes of testing, a later portion of a patient's breath which has come from an alveolar region of the lungs, rather than an earlier portion which has merely come from the mouth, trachea and bronchial passages. Thus, it is preferable to trap only the final portion of an exhalation in a sampling device.

A more specific object of the invention is to design a sample collecting device which is more reliable than known collecting devices in this respect in that when a patient blows into it, an initial portion of a patient's exhalation is able to pass straight through unimpeded, whereas a final portion can be held within the device.

With the aforesaid objects in view, the invention provides a breath sampling device comprising a hollow container defining a sample chamber and formed of at least two parts which fit together and have apertures therein, at least one of said parts being displaceable relative to the other part or parts between a first relative disposition of the parts in which the apertures are open so as to provide a clear path for air to pass through the container and a second relative disposition of the parts in which the apertures are closed so that there is no path for air to pass through and a volume of air is trapped in the chamber.

Preferred embodiments of the breath sampler of the invention consist of two hollow tubular parts that fit together with one part extending at least partially inside the other. The parts have apertures formed therein at such positions that when fitted together in one relative disposition there is a clear path for air to pass through the assembly and in another relative disposition there is no path for air to pass through and there is a volume of air trapped in the assembly. Transition from one relative disposition to the second relative disposition is achieved by relative movement of the two hollow parts with respect to each other, for example by rotation of one with respect to another, by relative linear movement or by bending.

However, an alternative embodiment may comprise a single tube having apertured end closures as well as rotatable end caps at each end.

Devices according to the invention preferably include, within the sample chamber, an indicator which is capable of providing a detectable indication of the presence of a given substance in a gas sample contained in said chamber.

The indicator within the chamber of the sampling device may suitably comprise any substrate carrying a material which provides a detectable indication of the presence of a given substance in a gas sample contained in the chamber.

The detectable indication is generally a change of colour and/or intensity, which change may lie in that part of the electromagnetic spectrum which is visible to the unaided human eye, or else it may be invisible in which case the indication will be detectable only with the use of additional optical or electro-optic equipment or under particular illumination conditions.

The invention will be described further, by way of example, with reference to the accompanying drawings, in which.

With reference to FIGS. 1 to 4, a preferred embodiment of the breath sampler of the invention comprises two cylinders 10, 20. The first cylinder 10 is open at one end and at the other it has an end closure 12 provided with an eccentrically located aperture 14. The second cylinder 20 has a similar end closure 22 with a similar eccentrically positioned aperture 24 at one end and its other end is also closed, in this case with a removable cap 28. The diameter of the second cylinder 20 is such that it fits snugly into the first cylinder 10 and its length is such that it is longer than the first cylinder 10. The second cylinder 20 is fitted inside the first cylinder 10 such that the end closures 12, 22 are adjacent each other at the same end.

Each cylinder 10, 20 also has a respective opening 16, 26 of similar size in its side walling. These respective openings 16, 26 are so placed that they line up when the cylinders 10, 20 are rotated relative to one another in order to line up the apertures 14, 24 in their end closures 12, 22 (in the open position) shown in FIGS. 1 and 3. In this disposition there is a clear path for air to pass through the end closure 12 of the first cylinder 10 and through the end closure 22 of the second cylinder 20 into the interior of the second cylinder 20 and then out again through the other openings 16, 26 at the sides of the cylinders 10, 20.

Figure 2:
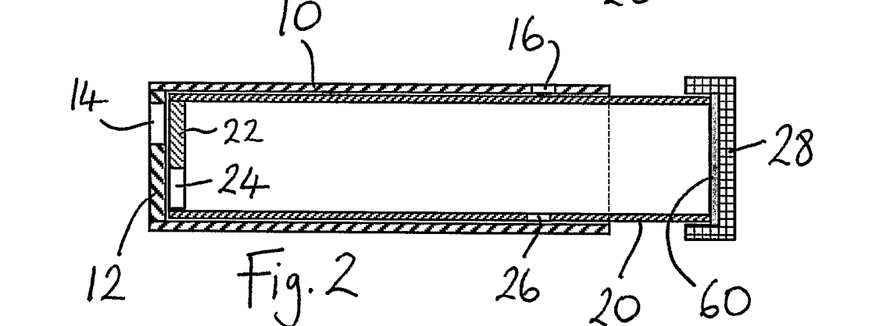
FIG. 2 is a similar view of the same embodiment in a second, closed configuration.
Figure 3:
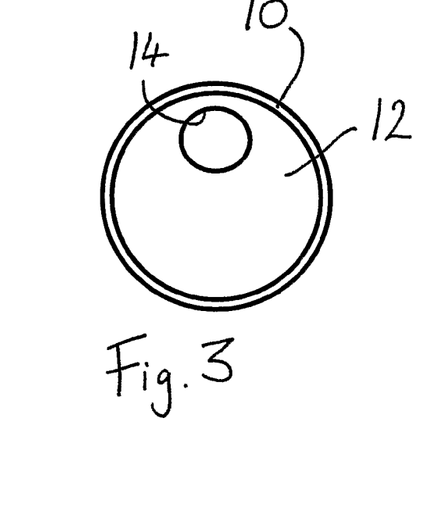
FIG. 3 is an end view, to an enlarged scale, of the same embodiment in the direction of arrow A and in the open configuration as shown in FIG. 1.
Figure 4:
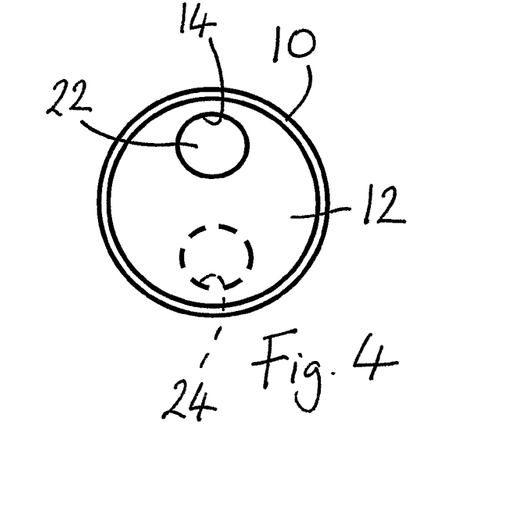
FIG. 4 is a similar view in the closed configuration shown in FIG. 2.

When the cylinders 10, 20 are then rotated relative to each other, e.g. the inner cylinder 20 rotated about 180° relative to the outer 10, to the disposition shown in FIGS. 2 and 4, there is no longer a passage for air to pass through the apertures 14, 24 at their ends 12, 22 and the other openings 16, 26 at their sides also do not line up. Consequently there is no passage for air to pass from the interior of the second cylinder 20 and a sample of atmosphere is trapped in the interior of the second cylinder 20.

Figure 1:
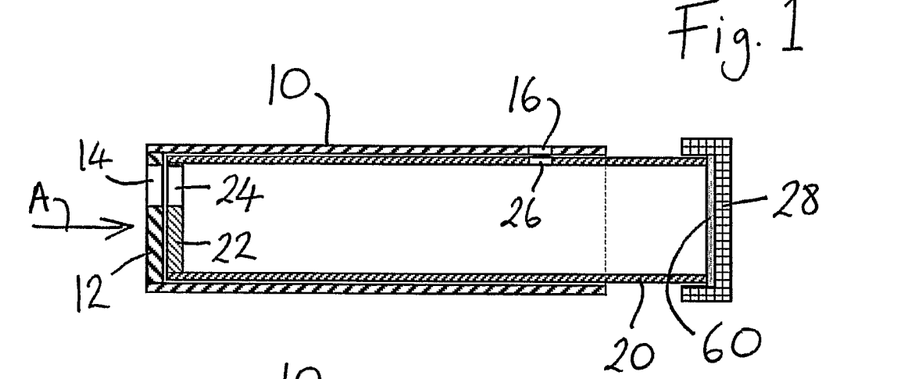
FIG. 1 is a longitudinal cross section through a first practical embodiment of a breath sampling device according to the present invention in a first, open configuration.

The end closure 12 with the aperture 14 of the outer cylinder 10 is so designed that it is compatible with disposable mouth-pieces that are currently used with medical equipment for spirometry.

Visible marks and/or respective formations, such as a protrusion and an indentation which interengage, may be provided on the cylinders 10, 20 to indicate the required relative positions for the open and closed conditions of FIGS. 1 and 2 respectively.

Figure 5:
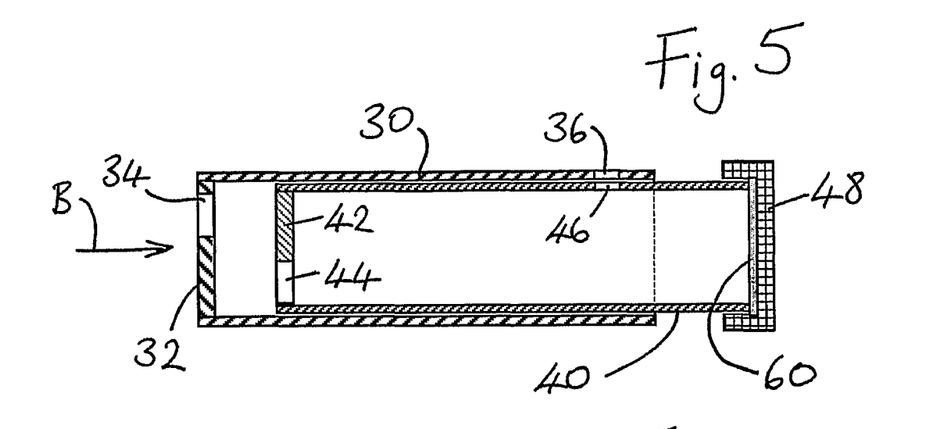
FIG. 5 is a longitudinal cross section of a second practical embodiment of a breath sampling device according to the present invention in a first, open configuration.
Figure 6:
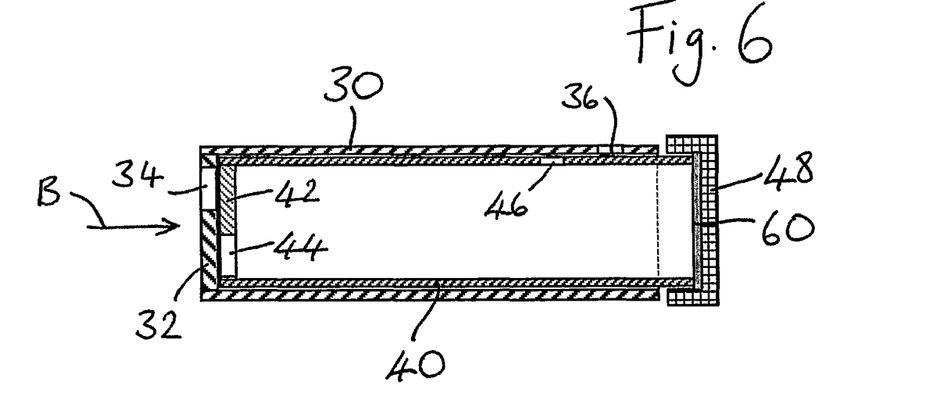
FIG. 6 is a similar view of the second embodiment in a second, closed configuration.
Figure 7:
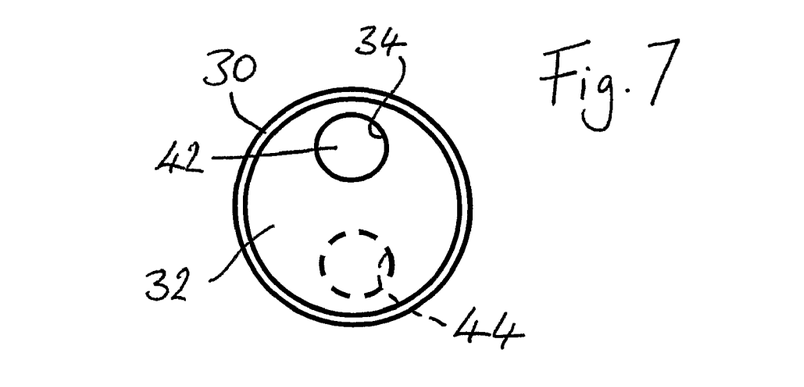
FIG. 7 is an end view, to an enlarged scale, of the second embodiment in the direction of arrow B shown in FIGS. 5 and 6.
Figure 8:
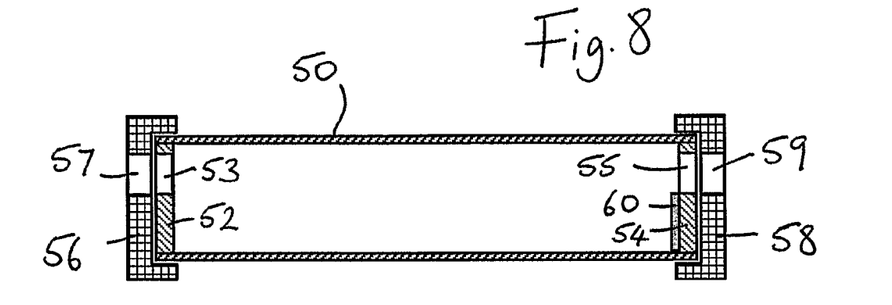
FIG. 8 is a longitudinal cross section of a third practical embodiment of a breath sampling device according to the present invention in a first open configuration.
Figure 9:
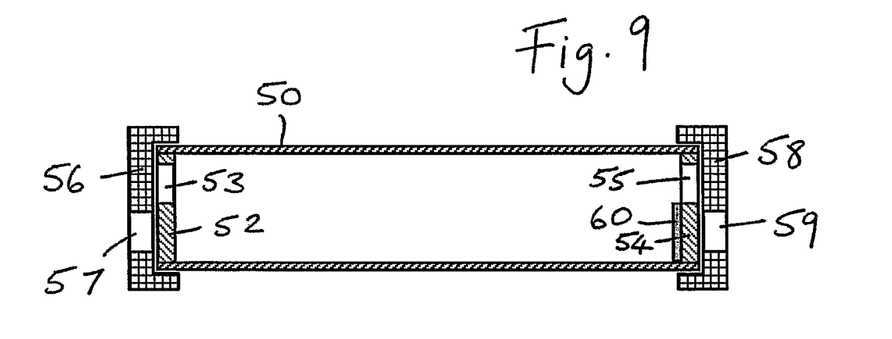
FIG. 9 is a similar view of the third embodiment in a second closed configuration.
Figure 10:
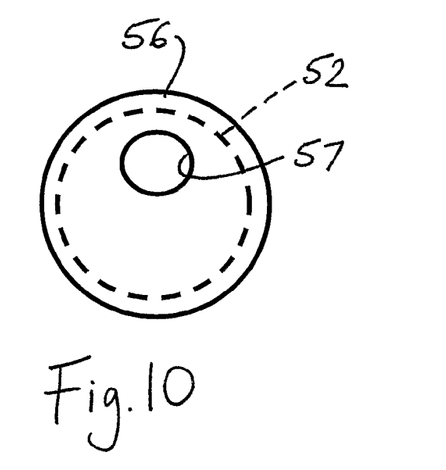
FIG. 10 is a view, to an enlarged scale, of either end of the open third embodiment in the configuration shown in FIG. 8.
Figure 11:
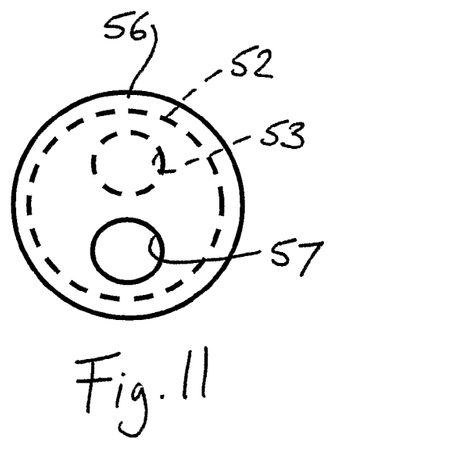
FIG. 11 is a view, to an enlarged scale, of either end of the third embodiment in the closed configuration shown in FIG. 9.

With reference to FIGS. 5 to 7, an alternative embodiment of a breath sampling device in accordance with the invention is also constructed of two cylindrical parts 30, 40, the second of which (40) is a close sliding fit within the first (30). Each cylinder 30, 40 has a respective end closure 32, 42 with an eccentrically positioned aperture 34, 44 therein and it also has a respective additional opening 36, 46 in its respective side walling. However, these side wall openings 36, 46 are so positioned that a clear path for air through the device can be obtained by moving the cylinders 30, 40 axially with respect to each other from the position shown in FIG. 6 (closed) to the position shown in FIG. 5 (open). Thus the device is opened once the inner cylinder 40 has been telescopically slid outwards relative to the outer cylinder 30, whereby the end closures 42 and 32 are brought apart to allow air passage through the non-aligned apertures 44 and 34. At the same time the opening 46 is brought into register with the opening 36. A removable end cap 48, similar to that (28) in the first embodiment, is also provided on the other end of the inner cylinder 40.

Again respective marks or formations may be provided on the cylinder 30, 40 to indicate at least their required relative position to align the openings 36, 46.

FIGS. 8 to 11 illustrate another possible embodiment of a breath sampler of the invention which consists of a single cylindrical container 50 fitted with respective non-rotatable captive closures 52, 54 at each end. These closures 52, 54 may be either removable or an integral part of the structure. Each closure 52, 54 has a respective eccentrically located aperture 53, 55 in it. Another two caps 56, 58 with respective matching eccentrically located apertures 57, 59 are placed over the respective end closures 52, 54, but these caps are free to rotate relative to the captive closures 52, 54 so that in the position shown in FIGS. 8 and 10 the apertures 53, 57 and 55, 59 at each end line up and in any other position they do not line up. Thus by rotating the outside caps 56, 58 at both ends it is possible to line up the apertures 53, 57 and 55, 59 so that there is a clear path for air to pass through the cylinder in the open position (FIG. 8) or it is possible to ensure that such a clear passage is not possible by rotation, e.g. by about 180° degrees, of the outer caps 56, 58 to the closed position, shown in FIGS. 9 and 11. In the latter, consequently, a sample of atmosphere is trapped inside the cylinder. One of the end caps 56 is so designed that it is compatible with disposable mouth-pieces that are currently used with the medical equipment for spirometry.

As before, marks or formations may be provided to help indicate the required cap positions for the open and closed condition of the device. In this case, such marks or formations will be on the cylinder 50 and the respective caps 56, 58.

Figure 12:
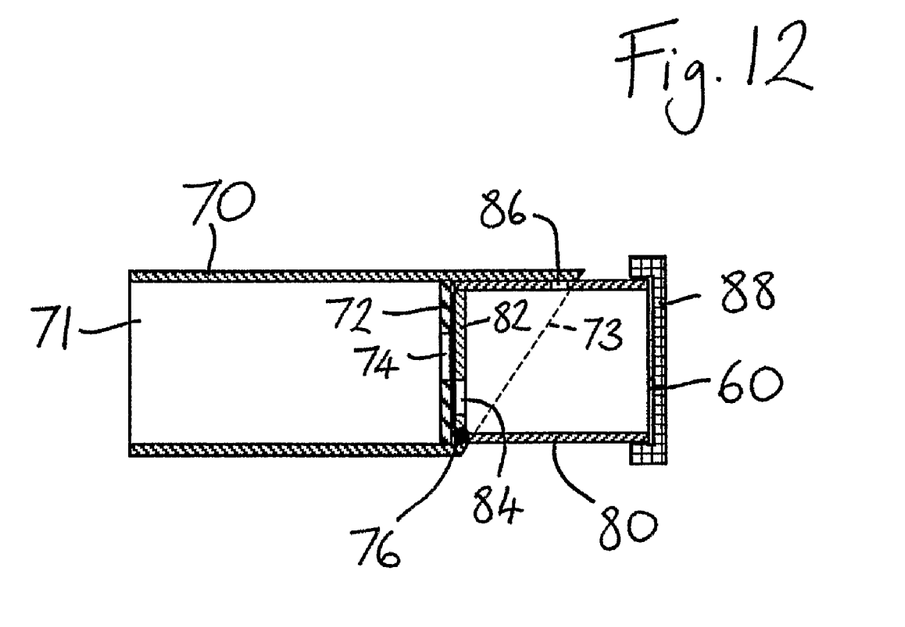
FIG. 12 is a longitudinal cross section of a fourth practical embodiment of the breath sampling device of the invention in a closed configuration.
Figure 13:
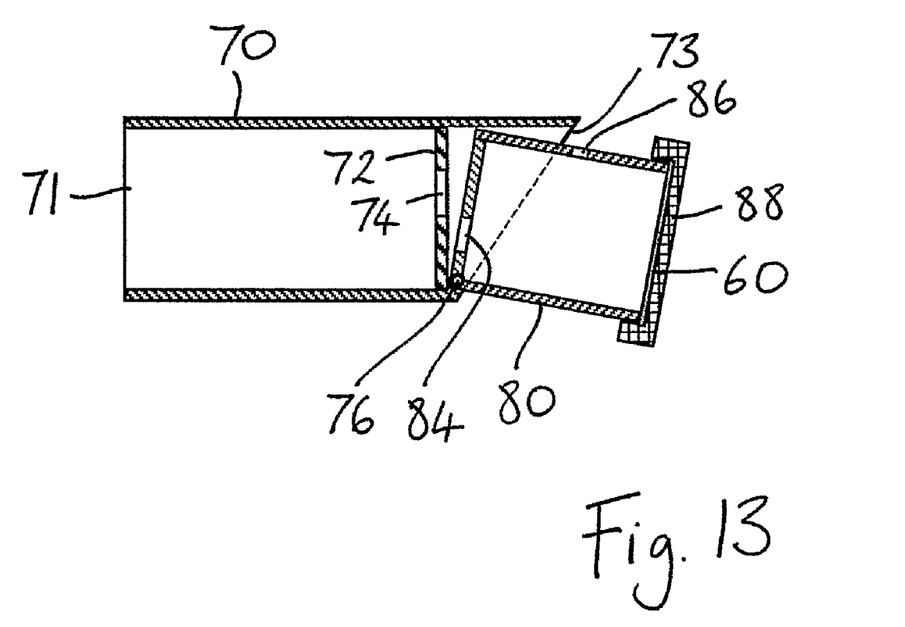
FIG. 13 is a similar view of the fourth embodiment in an open configuration.

Another embodiment of the breath sampler of the invention is illustrated in FIGS. 12 and 13. This again comprises two cylinders 70, 80 which are held in engagement with each other. The first cylinder 70 has an open, inlet end 71 for a patient to blow in to. Its other end is cut obliquely relative to the cylinder axis and an end closure 72 with an eccentric aperture 74 is provided just inside the shorter part of the oblique edge 73. The second cylinder 80 has an end closure 82 with an eccentric aperture 84 at one end, and a removable end cap 88 at its other end. The second cylinder 80 is of a slightly smaller diameter than the first cylinder 70 and fits into the end of the first cylinder 70 beyond the end closure 72, adjacent the oblique edge 73, so that the respective end closures 72, 82 lie next to each other, as shown in FIG. 12. The apertures 74, 84 are not in alignment in this position. There is an opening 86 in the side walling of the second cylinder 80, but in this position, it is covered by the longer part of the obliquely cut wall of the first cylinder 70. Accordingly, in this condition, the closed condition, there is no passage for air to pass through the container formed by the two cylinders 70, 80.

The second cylinder 80 is actually attached to the first cylinder 70 by a hinge arrangement 76 at the shorter part of the oblique edge 73. Therefore, the second cylinder 80 can be swung down about this hinge 76 to the position shown in FIG. 13 where the end closures 72, 82 are separated so that there is a passage through via the apertures 74,84, and where the opening 86 is also free of the walling at the longer side of the cylinder 70. Thus, in this open condition, air can flow freely through from the first to the second cylinder and outwards therefrom.

Yet another embodiment of the breath sampler of the invention is illustrated in FIGS. 14 to 18. This comprises two parts 90, 100, the second of which is mounted as a close sliding fit within the first and which is rotatable relative to the first in order, in a first disposition, to align apertures provided in the parts and open the device for through flow of air, and, in a second disposition, to close the apertures and trap air within the device. However, in this embodiment the parts 90, 100 are of a somewhat different form and fit together in a somewhat different manner compared to the preceding embodiments.

The first part 90 is a hollow elongate body which is rectangular in plan view (FIGS. 15 and 17) and substantially square in end view. It has a longitudinal axis 99.

Figure 14:
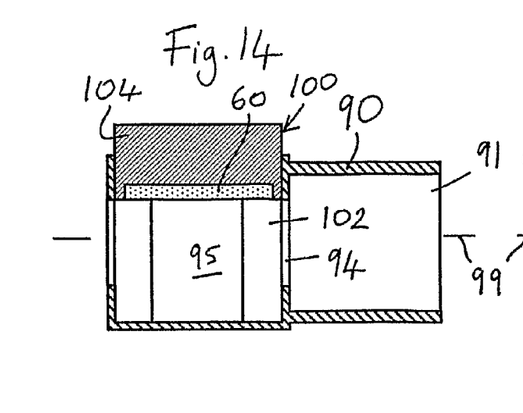
FIG. 14 is a longitudinal cross section of a fifth practical embodiment of the breath sampling device of the invention in an open configuration.
Figure 15:
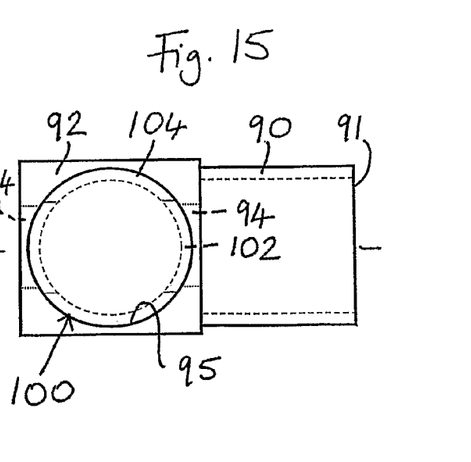
FIG. 15 is a plan view of same.
Figure 16:
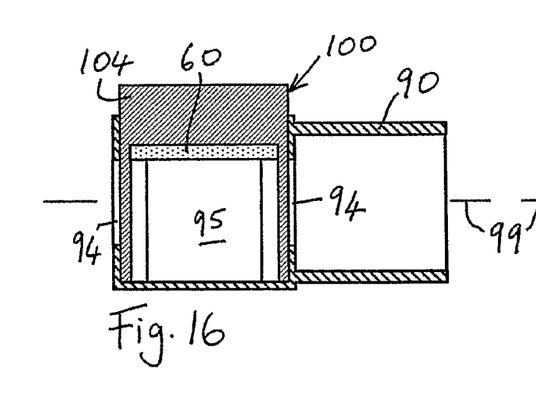
FIG. 16 is a view similar to FIG. 14 but showing this fifth embodiment of the device in a closed configuration.
Figure 17:
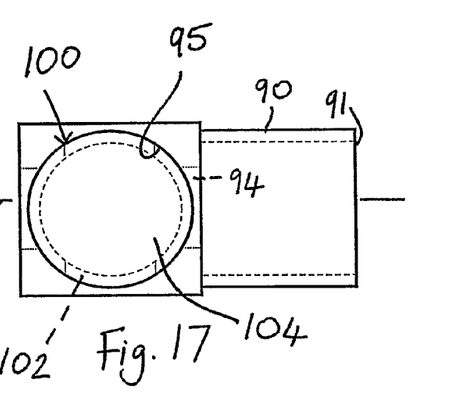
FIG. 17 is a plan view of same.
Figure 18:
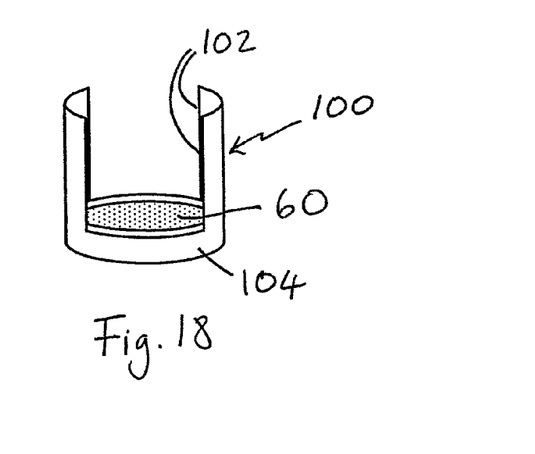
FIG. 18 is an inverted perspective view of the insert part of the embodiment shown in FIGS. 14 to 17.

At one end 91, the right hand side as seen in FIGS. 14 to 17, the body 90 is open. This end 91 is adapted to accept a standard mouthpiece (not shown) as used in spirometry. The other end of the body 90 is in the form of a block 92 provided with an axial through bore 94 communicating to the open end 91. This block 92 is also provided with a wide blind bore 95 perpendicular to the axis 99, providing, in effect, a socket in which the second part 100 is received, as best shown in FIGS. 14 and 16. The second part 100 is a rotatable insert, which itself is of hollow cylindrical form, as shown in FIG. 18. It has opposing slots 102 in its side walling, and an end wall 104 which projects beyond the mouth of the blind bore 95 to allow for manual rotation of the insert 100. Thus, the insert 100 is rotatable between the open position shown in FIGS. 14 and 15, where the slots 102 are aligned with the through bore 94 to allow air from end 91 to flow straight through, and the closed position shown in FIGS. 16 and 17 where the slots 102 are perpendicular to the bore 94 and there is no passage through the device. In this closed condition, air, specifically a breath sample, is trapped within the interior of the insert 100.

As before, marks or formations may be provided on the end wall 104 of the insert 100 and on the body 90 to indicate the open and closed positions of the insert 100.

Obviously, the specific details of the shape and configuration of the body and the insert may be modified in other embodiments. The body may, for example, be cylindrical instead of cuboidal in external shape. Also, the insert could be movable in and out substantially perpendicular to the axis of the body instead of being rotatable in order to align its apertures or through passage with respective apertures or through bore of the body or, alternatively to close these off.

It is preferred in all the above embodiments for the construction of the breath sampler to be such that in the closed condition the sample of breath is isolated from the surrounding atmosphere. In the closed condition the breath sampler need not necessarily completely prevent the passage of gas between its interior and exterior provided that the rate at which gas may flow outwards is sufficiently low that the amount of gas lost in this way is not great enough to affect the results obtained once samples have been collected.

In each of the illustrated embodiments an indicator 60 is mounted inside the respective container (10, 20; 30, 40; 50; 80; 90,100). The indicator 60 is made from a suitable substrate, such as paper, that is impregnated with curcumin, a substance that is known to change its colour when exposed to ammonia, but is not affected by other gaseous constituents of the healthy human breath.

The chemical name for curcumin is 1, 7-bis(4-hydroxy-3-methoxyphenyl)-1,6-heptadien-3,5-dione. It is the main compound responsible for the colour of turmeric and it undergoes a colour change from yellow to red brown on exposure to ammonia. It is insoluble in water, so is largely unaffected by moisture levels in the atmosphere or in a breath sample. It is soluble in ethanol and acetic acid and that is how it is applied to a paper substrate. In comparison to other substances which are used as colour change indicators for ammonia, it is not significantly affected by other substances commonly found in atmosphere or breath. Also, being a plant extract, it is relatively safe and not hazardous to the environment upon disposal. For these reasons it is a particularly suitable indicator substance for the present purpose.

In the preferred embodiments of FIGS. 1 to 7 and in FIGS. 12 and 13 the indicator 60 is mounted on the inside of the respective removable end cap 28, 48, 88 that is placed at the free end of the inner cylinder 20, 40, 80 of the breath sampler described above. The cap 28, 48, 88 is constructed so that when placed on the cylinder 20, 40, 80 only a central part of the indicator 60 is exposed to the sample of breath and the surrounding part, around the perimeter margin, is not so exposed. Thus, if ammonia is present in a significant detectable quantity, there should be a clearly defined boundary between the exposed and unexposed parts of the indicator 60 at the end of the sample collection procedure.

The human eye is more sensitive to assessing a difference in appearance, such as colour or colour intensity, than to judging an absolute state, even when compared with a colour chart of some sort. Therefore, with the arrangement just described, where only part of the indicator is exposed to the breath sample, any medically significant amount of ammonia should be visually apparent, even to an untrained or unskilled operative or the patient him/herself, because of the contrast in colour or intensity with the unexposed area. An unexposed, differently coloured boundary to the indictor makes visual detection especially easy.

In cases such as those just mentioned where the colour change resulting from the exposure of the indicator 60 to a breath sample containing ammonia is sufficiently pronounced that it can be observed by the naked eye, an optical reader is required only when it is desired to quantify the magnitude of the colour change. In other cases where the colour change is not large enough to be unequivocally determined by the naked eye a reader will always have to be used. The exposed indicator, or the exposed region of the indicator, is then presented to the input of the reader where it is illuminated by a light of specific wavelength. The amount of scattered and reflected light is detected by a suitable light detector and converted to an electrical signal. The magnitude of such signal is then compared to that obtained when the indicator was tested prior to being exposed to the sample of the captured breath.

In a preferred system, of which the sample collection device of the invention forms part, the cap 28, 48, 80 in which the indicator 60 is mounted is designed to fit snugly onto an opening on the optical reader where the indicator 60 needs to be placed for measurement as just described. Thus, there is no need for separation of the indicator 60 from its cap 28, 48, 80. Manipulation and handling of the indicator 60, which may be fragile, and which could lead to errors, is avoided. The indicator 60 is retained in the cap 28, 48, 80 while reading takes place.

In the embodiment of FIGS. 8 to 11, the indicator 60 and the end closure 54 may need to be carefully separated from the container 50 for visual inspection and/or application to the reader input.

In the embodiment of FIGS. 14 to 18, the indicator 60 is mounted inside the end wall 104 of the insert 100. This could be carefully removed for application to a reader input or the whole insert could be adapted to fit over the input or else the end wall, with indicator 60 still mounted thereto, could be separable for this purpose. Also, in this embodiment the indicator could be mounted in such a manner that its peripheral area is marked and left unexposed to a breath sample held within the interior of the insert 100.

The breath sampler of the invention, including, of course, the above described embodiments, may be formed from any suitable material, or materials, which do not interfere with any samples collected in it, or the indicators used, in a way which might affect results. For example, the material should not contain any additives which might render the indicator inoperative, provide a "false positive" result or impede sample gases from coming into contact with the indicator.

Preferably the breath sampler of the invention is made of paper and/or cardboard and/or plastics materials. The use of such materials should provide an economical device which is suitable for disposal after a single use. The device may comprise a single material, or may comprise a combination of materials, such as a laminate or more than one layer of the same or different materials.

It will be appreciated that the properties of the materials, eg thickness, basis weight etc. should be chose as appropriate with regard to the environmental conditions which the device must withstand in use. For example, the device should retain its integrity over the temperature and pressure ranges likely to be encountered, and over timescales from the collection of samples to the analysis of results, and over any period that the device may subsequently be stored.

The volume of the sample chamber within the breath sampler device is preferably in the range from 10 to 500 $cm^3$, most preferably 100 to 200 $cm^3$.

The breath sampler according to the present invention is advantageously constructed so as to be disposable after a single use preferably according to standard procedures, such as incineration or burial, without presenting a hazard to the environment.

The breath sampler of the invention is preferably biodegradable.

In use, a breath sampler device in accordance with any of the above described embodiments of the present invention, with an integral indicator 60, is firstly arranged in its open condition (FIGS. 1, 5, 8, 13 or FIGS. 14 and 15). A disposable mouthpiece (not shown) is attached to the relevant end of the breath sampler, which is the left hand end, as shown in the accompanying drawings, except in FIGS. 14 to 17. A patient breathes out through the disposable mouthpiece and the breath sampler. At the end of the patient's exhalation, the disposable mouthpiece is discarded and the breath sampler is immediately moved into the closed position. (FIGS. 2, 6, 9, 12 or FIGS. 16 and 17).

If required the procedure is repeated to obtain more then one "control" sample of breath.

After a period of time that is sufficiently long for any possible ammonia in the breath sample to induce changes in optical properties of the indicator (and a minimum period of about two minutes is probably sufficient), the indicator (in the case of FIGS. 8 to 11 and 14 to 18) or the cap containing the indicator (in the case of FIGS. 1 to 7 and FIGS. 12 and 13) is removed and presented to the reader (not shown). The reading thus obtained is referred to as the base reading. Obviously the aforesaid step is repeated if more than one base reading is required.

The patient is then administered an activating substance, eg ordinary unlabelled urea in a drink, and after a suitable period has elapsed to allow the ingested urea time to contact any *H. Pylori* in the gastro intestinal tract, a second breath sample is taken. This is tested for the presence of ammonia in the same way and the sample reading obtained compared with the base reading. If a patient is infected with *H. Pylori* bacteria, the second "test" sample obtained after ingestion of the activating substance would be expected to exhibit a greater quantity of ammonia than the "control" sample taken to establish the base level of ammonia in the patient's body.

The aforesaid method could also be employed without a reader in some circumstances, for instance as an initial test for a potential problem carried out in a doctor's surgery where there is no reader, by simple visual comparison of the indicator from the control and test samples. Once a positive or negative result is thus obtained, quantitative testing using an optical reader could be carried out later if required.

The foregoing is illustrative and not limitative of the scope of the invention. It will be understood by those skilled in the art that various changes in form and detail may be made within the scope of the invention and that any part of any embodiment already described could be used in combination with any part of another embodiment, or modified in some way.

As to the indicator, in other embodiments this could be incorporated into the structure of the inner cylinder or single cylinder body or any of the end closures or end caps which define the ends of the sample chamber within the container. Alternatively, it can be loosely placed in the said chamber where it is exposed to the trapped sample of patient's breath, and then removed for visual inspection or reading in a machine. Another possibility is that part of the indicator remains outside of the chamber to provide an unexposed part for more ready visual contrast as already discussed.

Obviously, other indicator substances (other than curcumin) may be used to detect the presence of ammonia by colour change or otherwise, and as these are known they need not be detailed here. Other substances (other than ammonia) may be tested for using the device of the invention, in which case the indicator will be chosen appropriately. Also, of course, the device of the invention is applicable more widely to collection of breath samples and for testing for conditions other than just *H. Pylori* infections by choice of appropriate indicators and associated methodology.

The invention claimed is:

1. A breath sampling device comprising a hollow container defining a sample chamber and formed of at least two parts which fit together and have apertures therein;

wherein at least one of said parts is displaceable relative to the other part or parts between a first relative disposition of the parts in which the apertures are open so as to provide a clear path for air to pass through the container, and a second relative disposition of the parts in which the apertures are closed so that there is no path for air to pass through and a volume of air is trapped in the chamber;

wherein the container comprises first and second tubular parts, each having side walling and respective end closures, the side walling of the first tubular part having an aperture therein and being a close fit within the side walling of the second tubular part, so that said side walling aperture is respectively uncovered and covered by the side walling of the second tubular part as the parts are moved between their first relative disposition and their second relative disposition; and wherein the respective end closures of the first and second tubular parts lie at a common end of the sample chamber and each end closure has at least one aperture therein which is opened and closed, respectively, as the parts are moved between their first relative disposition and their second relative disposition.

2. A device as claimed in claim 1 wherein the side walling of the second tubular part also has an aperture therein, the respective apertures in the side walling of the first and second parts being moved into and out of register as the parts are moved between their first relative disposition and their second relative disposition.

3. A device as claimed in claim 1 wherein the first and second tubular parts are cylindrical and relatively rotatable between their first relative disposition and their second relative disposition and the apertures in their respective end closures are moved into and out of alignment as the parts are so rotated.

4. A device as claimed in claim 1 wherein the first and second tubular parts are axially moveable relative to each other.

5. A device as claimed in claim 1 wherein the first tubular part is pivotable relative to the second tubular part so as to swing apart from the second part to move from the second relative disposition of the parts wherein the apertures are closed to the first relative disposition of the parts wherein the apertures are open.

6. A device as claimed in claim 1 further comprising, within the sample chamber, an indicator which is capable of providing a detectable indication, by change of color or color intensity, of the presence of a given substance in a gas sample contained in said chamber, the indicator being mounted inside the sample chamber in such a manner that only a part of the indicator is exposed to gas within the sample chamber and part thereof is unexposed so that there will be a boundary between the exposed and unexposed parts after the former has been held in contact with gas trapped within the chamber.

7. A device as claimed in claim 6 wherein the indicator is mounted inside the sample chamber in such a manner that only a central part thereof is exposed to gas within the sample chamber and a surrounding peripheral part thereof is unexposed.

8. A device a claimed in claim 7, wherein an end cap is provided on one of the tubular parts and the indicator is mounted inside the end closure and/or the end cap of the container.

\* \* \* \* \*